(12) United States Patent
Sachatello et al.

(10) Patent No.: US 6,976,992 B2
(45) Date of Patent: Dec. 20, 2005

(54) DUAL-FUNCTION MEDICAL INSTRUMENT

(75) Inventors: Charles R. Sachatello, Lexington, KY (US); Joseph Sawyer, Bozeman, MT (US)

(73) Assignee: SutureCut, LLC, Lexington, KY (US)

(*) Notice: Subject to any disclaimer, the term of this patent is extended or adjusted under 35 U.S.C. 154(b) by 327 days.

(21) Appl. No.: 10/196,493

(22) Filed: Jul. 16, 2002

(65) Prior Publication Data

US 2004/0015181 A1  Jan. 22, 2004

(51) Int. Cl.[7] .................. A61B 17/28; A61B 17/42; A61B 17/44
(52) U.S. Cl. .................. 606/205; 606/206; 606/207; 606/208; 606/210
(58) Field of Search .................. 606/174, 205, 606/207, 208, 206, 210; 30/194; 7/125, 132, 7/133, 134, 135, 153

(56) References Cited

U.S. PATENT DOCUMENTS

| | | | |
|---|---|---|---|
| 1,579,379 A | 4/1926 | Marbel | |
| 1,876,792 A | 9/1932 | Thompson | |
| 2,127,190 A | 8/1938 | Solomon | |
| 2,134,265 A | 10/1938 | Rosenfeld | |
| 2,305,156 A * | 12/1942 | Grubel | 403/114 |
| 2,315,326 A | 3/1943 | Gmeiner | |
| 2,394,807 A | 2/1946 | Robinson | |
| 2,434,831 A * | 1/1948 | Brandenburg | 606/120 |
| 2,652,832 A | 9/1953 | Castrovicjo | |
| 2,885,781 A | 5/1959 | Baner | |
| 2,998,649 A | 9/1961 | Miller et al. | |
| 3,166,071 A | 1/1965 | Mayer | |
| 3,443,313 A | 5/1969 | Profy | |
| 3,763,860 A | 10/1973 | Clark | |
| 3,805,792 A | 4/1974 | Cogley | |
| 3,840,017 A | 10/1974 | Violante | |
| 4,271,838 A | 6/1981 | Lasner et al. | |
| 4,369,787 A | 1/1983 | Lasner et al. | |
| 4,375,218 A | 3/1983 | DiGeronimo | |
| 4,392,494 A | 7/1983 | Ashby | |
| 4,446,866 A | 5/1984 | Davison | |
| 4,452,246 A | 6/1984 | Bader et al. | |
| 4,478,221 A | 10/1984 | Heiss | |
| 4,669,470 A | 6/1987 | Brandfield | |
| 4,848,341 A | 7/1989 | Ahmad | |
| 4,938,214 A * | 7/1990 | Specht et al. | 606/174 |
| 4,949,717 A | 8/1990 | Shaw | |

(Continued)

FOREIGN PATENT DOCUMENTS

DE            91 05 152         9/1991

OTHER PUBLICATIONS

Scanlan International Surgical Instrumentation Catalog, copyright 1991, 1988, 1986 Scanlan International, Inc., pp. 37-38, 40-44, 55-76, 95-96, and 99-102.

(Continued)

*Primary Examiner*—Glenn K. Dawson
*Assistant Examiner*—Michael Mendoza
(74) *Attorney, Agent, or Firm*—Kilyk & Bowersox, P.L.L.C.

(57) ABSTRACT

A dual-use medical instrument is disclosed. In one embodiment, the instrument has a first handle pivotally attached to a second handle through a mortise and tenon joint to define opposing jaws at the distal end of the surgical instrument, each of the opposing jaws including a distal gripping portion, at least one longitudinally disposed cutting edge situated between the distal gripping portion and said mortise and tenon joint, wherein at least one longitudinal cutting edge is adjacent to said mortise and tenon joint. The instrument can function as a combination needle holder and surgical scissors.

29 Claims, 3 Drawing Sheets

U.S. PATENT DOCUMENTS

| | | | |
|---|---|---|---|
| 4,969,893 A | | 11/1990 | Swor |
| 5,002,554 A | | 3/1991 | Korber |
| 5,152,774 A | * | 10/1992 | Schroeder .................. 428/457 |
| 5,178,624 A | * | 1/1993 | Kyun .......................... 606/120 |
| 5,196,023 A | | 3/1993 | Martin |
| 5,219,354 A | * | 6/1993 | Choudhury et al. ........ 606/174 |
| D353,672 S | | 12/1994 | Swor |
| 5,385,569 A | | 1/1995 | Swor |
| 5,403,346 A | | 4/1995 | Loeser |
| 5,417,701 A | | 5/1995 | Holmes |
| 5,431,674 A | | 7/1995 | Basile et al. |
| 5,439,471 A | | 8/1995 | Kerr |
| 5,584,845 A | * | 12/1996 | Hart ........................... 606/174 |
| 5,601,575 A | | 2/1997 | Measamer et al. |
| 5,624,454 A | | 4/1997 | Palti et al. |
| 5,632,753 A | | 5/1997 | Loeser |
| 5,797,919 A | | 8/1998 | Brinson |
| 5,903,966 A | | 5/1999 | Sonderegger |
| 5,927,052 A | * | 7/1999 | Nippes et al. ................ 53/445 |
| 5,954,733 A | | 9/1999 | Yoon |
| 5,957,937 A | | 9/1999 | Yoon |
| 5,984,932 A | | 11/1999 | Yoon |
| 5,984,938 A | | 11/1999 | Yoon |
| 5,997,548 A | * | 12/1999 | Jahanger ..................... 606/120 |
| 6,024,744 A | | 2/2000 | Kese et al. |
| 6,051,004 A | * | 4/2000 | Gill ............................. 606/147 |
| 6,063,096 A | | 5/2000 | Boebel et al. |
| 6,146,399 A | * | 11/2000 | Lee ............................. 606/167 |
| 6,159,224 A | | 12/2000 | Yoon |
| 6,159,233 A | | 12/2000 | Matsuzawa |
| 6,217,592 B1 | | 4/2001 | Freda et al. |
| 6,224,614 B1 | | 5/2001 | Yoon |
| 6,234,327 B1 | | 5/2001 | Reed |
| 6,254,620 B1 | | 7/2001 | Koh et al. |
| 6,325,568 B1 | | 12/2001 | Druckman et al. ......... 403/282 |
| 6,334,861 B1 | * | 1/2002 | Chandler et al. ............. 606/50 |
| 6,355,035 B1 | | 3/2002 | Manushakian ............... 606/50 |
| 2002/0049470 A1 | * | 4/2002 | Fogarty et al. ............. 606/205 |

OTHER PUBLICATIONS

Instrumentation Cross-Reference, V. Mueller, sections 1-10.
Tisco Surgical Instruments, Catalog 2001, combination Needle Holder and Suture Scissors listed, Olsen-Hegar pp. 5, 17, 18.
Wexler Surgical Supplies Catalog, Suture Scissors and Needle Holders.
AESCULAP Catalog, AESCULAP AG & Co. KG, pp. 68-146 and 270-304.
Allen Surgical Co. Allen Surgical Instruments, Needle Holder and Suture, K062 Olsen Hegar Needle Holder 14cm.
Jorvet Catalog, General Surgical Instruments XV, pp. 77-81.
Suture Scissors at http://www.widgetsupply.com/images/ht-hemo-BB48.jpg.
Spectrum Surgical Instrument Products, copyright 1999-2002 Spectrum Surgical Instruments Corp.
Miltex OR Grade Carb-N-Sert T-C Needle Holders, Miltex OR Grade Olsen-Hegar T-C Needle Holders, and Miltex OR Grade T-C Needle Holders from www.medicalmailorder.com.
Ethicon a Johnson & Johnson Company, Miltex OR Olsen-Hegar Neddle Holders combined with Suture Scissors.
TC Instruments, Needle Holder with Tungstem Carbide Inserts.
Needle Holders, Olsen-Hegar needle holder & scissors combined with Gillies needle holder & scissors combined.
Gillies Combo Tungsten Carbide Needle Holders, Gillies Combo Tungsten Carbide Needle Holder & Scissor, copyright Anthony Products, Inc. 2001.
Eur J Plast Surg 22:338-339. copyright Priv.-Doz. Dr. med. Randolf Riemann 2000, Combined micro needle holder and microscissors.
Perfectra Surgical Instruments-Needle Holders, Perfectra Instruments.
Mayo-Hegar needle holders, Needle Holder-Mayo-Hegar, delicate pattern, copyright 2002 Fine Science Tools Inc.
Blue Lake Products, Needle Holders.
Sontec Instruments.com, Specialized Surgical Instruments, Webolutions, Inc.
Sur-Med Instruments, Inc., Surgical Instrument repair service.
Scissors, copyright 2000 Padgett Instruments, Inc.
Miltex Surgical Instruments, Miltex Instrument Company, Inc., copyright 1996, pp. 112-131.
Katena eye instruments catalog, http://www.katena.com/html/search_results.cfm?ProductType=12.
Sklar Surgical Instruments, Olsen-Hegar Needle Holder, http://www.sklarcorp.com/products/needleholders/olsenhegar.htm.
Sklar Surgical Instruments, Needle Holders, http://www.sklarcorp.com/products/nh.htm.
Robbins Instruments, Needle Holders, http://www.robbinsinstruments.com/needle-holders/needlehome.htm.
Allen Surgical Co., Dental Instruments.
Davis-Lobdell Instruments, Inc., http://www.davis-lobdell.com/products.html.
Open Directory, http://dmoz.org/Business/Industries/Healthcare/Products_and_Servic . . . Needle Holders, Gilles needle holder & scissors.
Needle Holder search results, www.medline.com.
AESCULAP, Surgical Instruments for Special Disciplines, copyright 1996-2001 AESCULAP AG & Co.KG May 17, 2001www.surgical-instruments-usa.info.

* cited by examiner

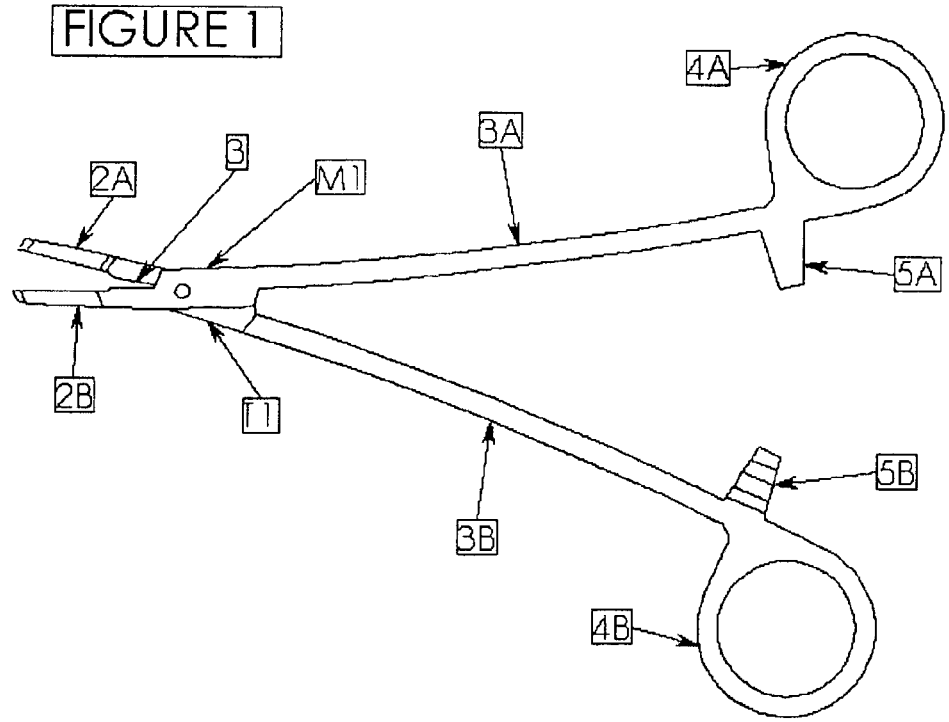
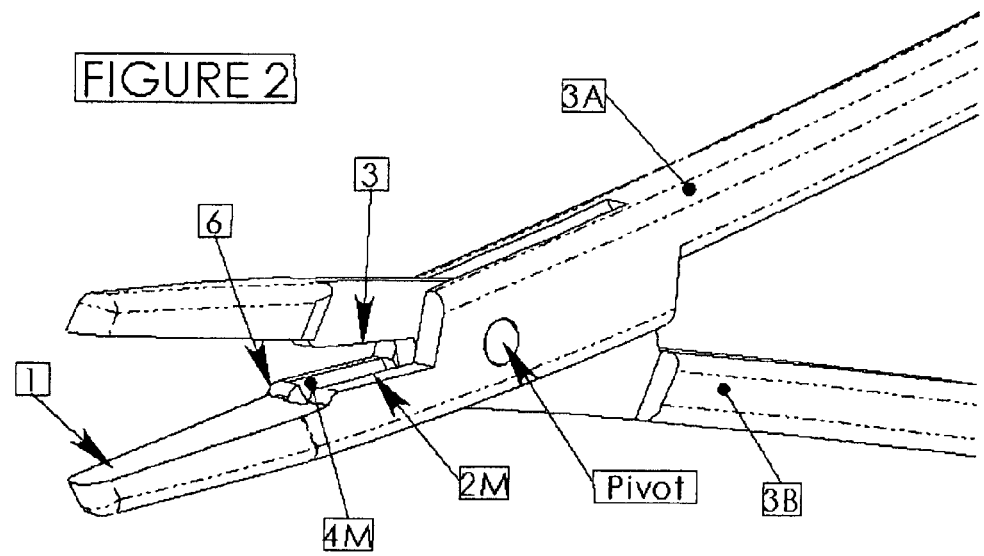

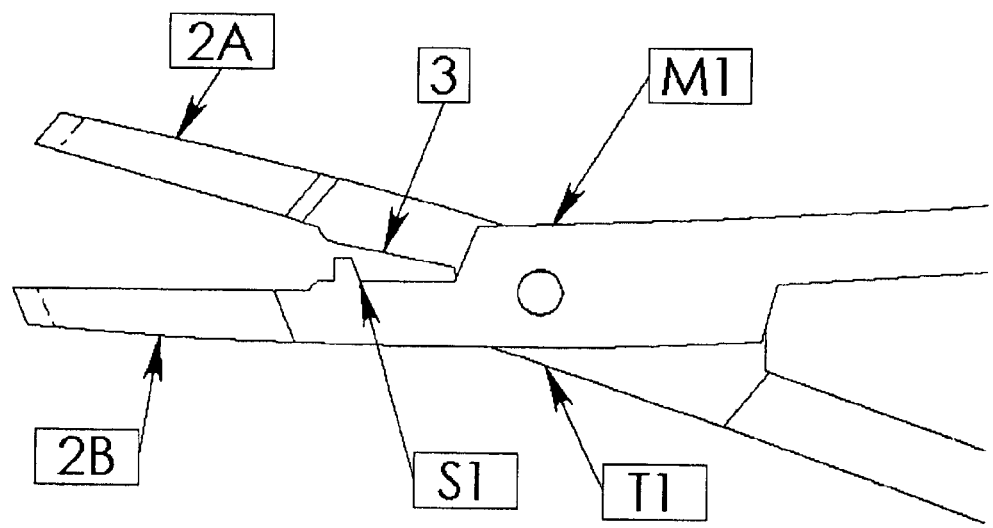

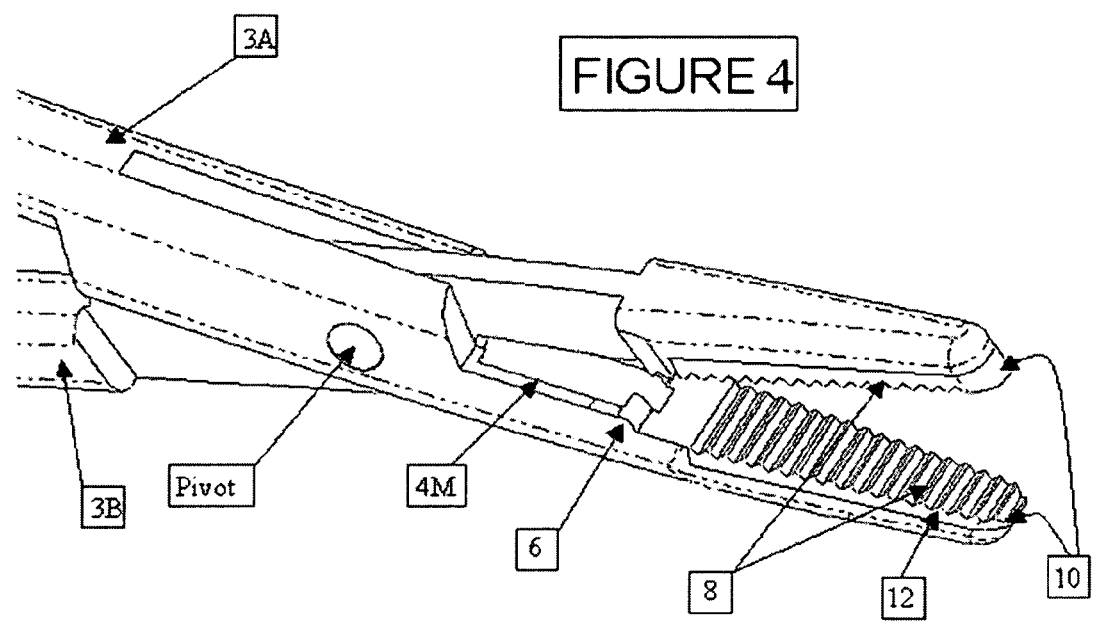

DUAL-FUNCTION MEDICAL INSTRUMENT

BACKGROUND OF THE INVENTION

The present invention relates to a dual-function medical instrument that combines the general functions of a needle holder and scissors. The present invention also relates to a dual-function instrument that does not present a cutting surface during the normal process of passing a surgical needle through tissue, but does allow the operator to selectively manipulate the instrument so as to be able to sever a surgical suture. The present invention also related to an instrument allowing a surgeon to place and trim surgical sutures without having to change instruments.

Since its inception, surgery has always involved the precise placement of sutures. The act of suturing is fundamental to the successful connection of one piece of tissue to another piece of tissue. Common example include such procedures as the closing of major incisions, repair of skin lacerations, or re-anastamosing blood vessels or segments of intestines.

In a typical example, a suture is mechanically connected to a surgical needle, which is firmly held in gripping instruments resembling elongated pliers, generally called "needle holders," "needle drivers," or "forceps," and all of these terms can be considered to be functionally equivalent. The surgical needle is passed through the two pieces of tissue with the aid of the needle holder and the suture follows the path of the surgical needle. After the suture has been passed through the two pieces of tissue that the surgeon wishes to connect, the suture must be tied into a knot and the ends must be trimmed. For decades, surgical scissors have been used to trim or cut sutures after tying, because scissors can trim or cut without placing any tension on the suture knot placed in the tissues to be joined. This lack of tension in the trimming process is of paramount importance because the tissues to be joined by the surgical procedure are often extremely delicate, especially in applications such as blood vessel surgery, and any tension on the surgical knot might cause the suture to tear through the delicate tissues.

In a typical surgical procedure, many sutures must be placed. For instance, in trauma surgery, sometimes hundreds of sutures must be placed. The operator must either change instruments after every suture is placed, replacing the needle holder with a scissors, or use an assistant to operate the scissors when placing multiple interrupted sutures. Even in the best of cases, this can be a laborious process, but it can easily be appreciated how cumbersome and laborious such a procedure must be in the case of major surgery. Additionally, because of the frequently unavailability of trained personnel and the costs inherent in using skilled assistants, the surgeon is frequently required to work alone without assistance to repair wounds. This latter situation is particularly common in the emergency rooms and doctor's offices and clinics today, as well as in the practice of veterinary medicine, which sometimes may take place in open fields, particularly in the case of large farm animals.

In these situations, the operator is required to change instruments often. In other words, the surgeon must change from scissors to a needle holder after each and every suture is placed. In many cases, each suture must be cut twice. The first cut is necessary to remove the needle from the suture when the suture has been joined mechanically to the needle, and a second time to cut the suture after it has been tied. This very act of changing one instrument for another is cumbersome, time consuming and costly as one or the other instrument can slide off the sterile operative field, requiring the use of additional sterile instruments with their attendant cost. Obviously, in some circumstances, additional sterile instruments may not be available readily, particularly in veterinary practice or in much of the developing world.

A variety of instruments and devices have been proposed and patented to provide the dual function of needle holder and scissors in a single instrument. The overall desirability of such a dual device instrument was cogently expressed by Gmeiner as early as 1940s, and his description of the problems inherent in using two instruments during surgery in the patent issued to him is still relevant today (U.S. Pat. No. 2,315,326).

The present invention is a surgical instrument combining the separate functions of two distinct instruments, one, a needle holder, facilitating the precise placement of sutures, and the second, a scissors, safely cuts suture material without putting any tension on the tissue sutured. This dual function instrument can reliably accomplish both functions without the necessity of the operator repetitively changing instruments from needle holder to scissors throughout the course of surgery, while minimizing the potential to unintentionally cut tissue, or the necessity to use a separate scissors instrument. In other words, the combination needle holder and suture scissors herein described permits the operator to both precisely place the needle and attached suture in tissue, tie a surgical knot with an instrument tie and then cut the suture without putting any tension on the sutured tissue, all without the necessity of changing instruments or using a separate scissors to cut the suture.

However, unlike conventional instruments, such as described in Gmeiner, the present invention does not present a cutting surface in normal usage, particularly when the needle holder is grasping a surgical instrument, such as a surgical needle. The drawback of other dual function instruments, such as Gmeiner, is that an exposed cutting surface is exposed any time the jaws of the instrument are not completely closed. Obviously, a grasping type Instrument cannot remain in fully closed configuration and fulfill its intended purpose. However, when such instruments are opened, the presence of an exposed cutting edge becomes extremely problematic. Given the delicacy of many anatomical structures, any sharp edges are extremely dangerous in a surgical instrument. Even if the edges are not moved towards one another in a cutting motion, many types of tissue, particularly blood vessels, can be damaged by any contact with a sharp edge. And once damaged, some tissues, such as blood vessels, cannot be repaired easily, if at all, and this may cause fatal consequences. Therefore, preventing such inadvertent damage is of paramount concern in surgery. The present invention overcomes the drawbacks of previous designs in that it combines the dual functions of needle holders and scissors, but does not present a sharp edge until the jaws are spread far apart.

All the patents and publications mentioned above and throughout are incorporated in their entirety by reference herein.

SUMMARY OF THE PRESENT INVENTION

A feature of the present invention relates to a dual-function medical instrument that combines the functions of needle holder and scissors.

Another feature of the present invention relates to a dual-function instrument that preferably does not present a cutting surface during the normal operation of passing a surgical needle through tissue, but does allow the operator to selectively manipulate the instrument so as to be able to sever a surgical suture.

A further feature of the present invention relates to an instrument allowing a surgeon to place and trim surgical sutures without having to change from one instrument to another.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a dual function medical instrument, as more particularly described below.

The medical instrument combines the functions of a separate needle holder and surgical scissors. In one embodiment, the instrument includes a first handle pivotally joined by a mortise and tenon joint to a second handle to define opposing jaws at or toward the distal end of the instrument. Each of the opposing jaws can meet to hold an item, such as to hold a surgical needle and attached suture firmly and securely between two distal gripping portions, so as to facilitate the passage of the needle through the tissue to be sutured. The instrument may have both finger handles to facilitate its use and may incorporate a locking ratchet mechanism to hold the needle in place, without pressure on the handles by the operator.

The use of this instrument eliminates the present necessity of the surgeon being forced to repetitively change instruments during the course of closing a wound. The ability to use one instrument to do the work of two separate instruments reduces the time necessary to close many wounds, the length of anesthesia necessary for the completion of the surgical procedure, and the added cost entailed by the contamination of the needle holder or scissors as they slide off the sterile surgical field, or are dropped in the act of picking one or the other up on a repetitive basis. However, unlike previous instruments, the present invention preferably does not present a cutting surface during the normal operation of passing a surgical needle through tissue, but does allow the operator to selectively manipulate the instrument so as to be able to sever a surgical suture. Various embodiments of the instrument are further described that offer specialized features important to surgeons.

It is to be understood that both the foregoing general description and the following detailed description are exemplary and explanatory only and are intended to provide a further explanation of the present invention, as claimed.

BRIEF DESCRIPTION OF THE DRAWINGS

The invention may be more fully understood with reference to the accompanying figures. The figures are intended to illustrate exemplary embodiments of the present invention without limiting the scope of the invention.

The accompanying figures, which are incorporated in and constitute a part of this specification, illustrate several embodiments of the present invention and together with the description, serve to explain the principles of the present invention.

FIG. 1 is a side view of one embodiment of the present invention described herein, namely that of a combination needle holder and suture-cutting instrument.

FIG. 2 is an angle view of the distal end of one embodiment of the present invention describe herein showing the mortise and tenon joint and a longitudinally displaced cutting edge.

FIG. 3 is a side view of one embodiment of the invention showing the distal end of the instrument and the positioning of the stop block in relation to other features of the instrument.

FIG. 4 is an angle view of the distal end of one embodiment of the present invention described herein showing the mortise and tenon joint and a longitudinally displaced cutting edge and further showing complementary needle receiving teeth or serrated teeth, as well as the optional replaceable inserts.

DETAILED DESCRIPTION OF THE PRESENT INVENTION

The present invention relates to a dual function medical instrument. One embodiment of the present invention is shown in FIG. 1, which illustrates a medical instrument that may be used as a combination needle holder and suture-cutting instrument. This instrument incorporates a first handle 3A pivotally attached to a second handle 3B through a mortise and tenon joint. The mortise and tenon parts of the joint are respectively identified, M1 and T1, and are held together by a conventional pin, screw, rivet, or other attachment means. As can be appreciated from FIG. 1, one of the handles contains the mortise M1 and the other handle contains the tenon T1. As can be seen from FIG. 1, the tenon T1 is defined as the portion of one handle that fits through an opening in the other handle, which is defined as the mortise M1, to form the mortise and tenon joint.

Each handle preferably includes an elongated portion extending proximally from the mortise and tendon joint. The first handle 3A and second handle 3B define a pair of opposing jaws 2A and 2B at the distal end or near the distal end of the instrument. Each of the opposing jaws 2A and 2B includes a distal gripping portion 3 thereon, designed to securely hold, for instance, a suture needle or other similar surgical device when the handles are approximated towards one another. The first and second handles may preferably include finger loops at the proximal end of the instrument 4A and 4B. Such finger loops make it easier for the user to operate the instrument, and may come in various sizes. Additionally, the first handle 3A and second handle 3B may preferably include opposing locking mechanisms, 5A and 5B. These locking mechanisms (e.g., releasable locking mechanism) can be any design that allows the opposing jaws to remain in a closed position. For instance, the opposing locking mechanism can be opposing teeth that rachet into place upon closing. The same locking mechanisms used in conventional needle holders can be used herein. For instance, these opposing locking mechanisms, 5A and 5B allow a user to lock the opposing jaws 2A and 2B on an metal object, such as a surgical needle. This is sometimes useful in surgery, so that a needle can be held securely, without any pressure from the hands of the surgeon.

Re-approximating the opposing jaws 2A and 2B allows a user to grasp a surgical needle or other object between the distal gripping portion 1 located on each of the respective jaws. The size of the distal gripping portion can be of any size, and may vary depending on the specific surgical function for which the instrument is designed, and preferably would be from about 1 centimeter to about 20 centimeters or more. As will be appreciated by a person skilled in the art, the exact shape and configuration of the distal gripping portions can be modified to suit particular applications. The distal gripping portions can have any surface texture and shape, such as complementary teeth to grip objects. For instance, the distal gripping portions can include a complementary needle receiving teeth, specially designed to grip a surgical needle (see FIG. 4 complementary needle receiving teeth 8). The distal gripping portions can include or comprise replaceable inserts. For instance, some replaceable inserts have fine teeth and other have rough surfaces made of other materials, including composite materials or diamond dust (see FIG. 4, replaceable inserts 10).

Alternatively, the distal gripping portions might also include serrated teeth, capable of firmly gripping a general metal object, or performing a clamping or crushing function, of performing any other function that might occur to a person skilled in the relevant art (see FIG. 4, serrated teeth 12). Appropriate design of the distal gripping portion 1 allows the instrument to be used for a wide variety of gripping functions, and the present invention is not merely limited to gripping surgical needles.

One embodiment of the suture-cutting portion of the present invention is shown in FIG. 2. The longitudinally disposed cutting edge 3 is formed on a projection of the tenon T1, and is adjacent to the mortise and tenon joint itself. The precise geometry of the cutting edge can be any cutting shape and, for instance, can be angled or serrated. As the first and second handles 3A and 3B are brought together, the longitudinally disposed cutting edge 3 fits into an aperture 4M.

As can be appreciated from FIG. 2, the longitudinally disposed cutting edge 3 is adjacent to the mortise and tenon joint and fits within the aperture 4M when the opposing jaws 2A and 2B are closed or even spread apart enough to grip a surgical needle or other object. Preferably, only when the opposing jaws 2A and 2B are spread widely apart does the cutting surface of the longitudinally disposed cutting edge 3 retract from the aperture 4M a sufficient distance to expose the cutting surface or edge.

In normal suturing operations, a surgeon can grasp a surgical needle or similar metal object without the longitudinally disposed cutting edge 3 fully projecting or retracting from the aperture 4M. A very small portion of the cutting edge may be exposed. This means that no cutting surface is exposed during the normal procedure of grasping a needle or passing the needle through tissue. This means that the user can perform suturing without the danger of exposing sensitive or delicate tissue to a cutting edge. However, once the suture is tied off, and it becomes necessary to trim the ends of the suture, the user can spread the first and second handles 3A and 3B further apart, thus exposing the longitudinally disposed cutting edge 3, and allowing the suture to be trimmed or severed, by closing the first and second handles 3A and 3B. Since the first and second handles 3A and 3B are generally spread widely apart to expose a sufficient cutting surface, the user is aware from the angle of the handles, as well as from visual examination of the instrument, when the cutting edge is exposed. Therefore, the user can easily monitor the exposure of the longitudinally disposed cutting edge 3 as it retracts from the aperture 4M.

Additionally, the design of the instrument ensures that when the jaws are only slightly spread to grip a surgical needle, or other object, essentially no sufficient cutting edge is exposed, and the user does not even need to monitor the exposure of the cutting edge. Therefore, a user can perform the delicate work of passing a needle through tissue without the fear of damaging sensitive structures through an inadvertent contact with a cutting edge. However, upon tying off the suture, the user can then spread the first and second handles 3A and 3B sufficiently apart, thus exposing the cutting edge, and allowing the suture to be trimmed, without the necessity to put down the needle holder and pick up a pair of scissors. Additionally, the shearing action of the present invention can be accomplished without putting any tension on the suture or the tissue joined by the suture, thus mimicking the action of an independent scissors instrument.

The present invention thus permits a user to perform the act of setting, holding or passing a needle to join tissue(s) and the act of severing of the suture material or thread in one and the same hand without the necessity of using a separate scissors instrument, or having an assistant cut the suture material with suture scissors. Therefore, the present invention allows users to perform suturing faster with less wasted motion. This is important in all types of surgery, but is particularly important in those instances in which the surgeon must work alone, without the aid of an assistant, such as in emergency practice, or in veterinary surgery, or in the practice of trauma surgery, where hundreds of sutures sometimes must be set.

At least one cutting edge is present for the invention to perform its intended purpose. For instance, in the embodiment depicted in FIG. 2, the longitudinally disposed cutting edge 3 is formed on a projection of the tenon T1. The edges of the aperture 4M can be sharp to be a second cutting edge or can be a non-cutting edge.

Alternatively, in another embodiment, additional longitudinal cutting edges could be present on either side of the aperture 4M. These additional longitudinal cutting edges 2M can be on either or both sides of the aperture 4M, thus producing optional two additional cutting edges, which extend past the longitudinally disposed cutting edge 3 when the first and second handles 3A and 3B are closed. Furthermore, the longitudinally disposed cutting edge 3 is formed on a projection of the tenon TI, and, consequently, may be on only one side of the projection, or on both sides. Therefore, depending on the specific embodiment, two additional longitudinal cutting edges 2M can be formed on either or both sides of the aperture 4M, and the longitudinally disposed cutting edge 3 can be formed on either or both sides of the projection of the tenon T1, thus producing two to four cutting edges. Also, edge 3 can be a non-cutting edge and one or both of the edges 2M on either side of the aperture can be a cutting edge.

An embodiment with two cutting edges on both sides of the aperture 4M, or on both sides of the projection of the tenon T1, may be less desired in that it would cut the suture into three portions, thus producing the potential of an additional foreign body residue (suture chaff) in the tissue being sutured or remaining in the joint mechanism itself. However, depending on the type of suture material (some types of material are non-toxic and biodegradable), and the type of surgery being performed, this embodiment might still be quite acceptable.

In another embodiment, only two longitudinally disposed cutting edges oppose one another and are optionally offset to extend past one another in a cutting geometry when the first and second handles 3A and 3B are closed. This embodiment involves producing a sharp edge on only one side of the aperture 4M and optionally a slight gap on the other side of the aperture 4M. In other words, the longitudinally disposed cutting edge 3 formed on a projection of the tenon T1 meets and extends past only one side of the aperture 4M in a cutting alignment. This would ensure that the suture is cut into only two pieces, and would eliminate the suture chaff discussed earlier. This configuration could be achieved by notching either the projection of the tenon T1 or the aperture 4M, so that a gap is produced on one side of the aperture 4M when the instrument is closed. In other words, if the instrument is closed, and the view in FIG. 1 is rotated 90 degrees along its axis, so that one is looking directly "down" on the instrument, one will be able to see through a small gap created where the projection of the tenon T1 or the aperture 4M do not meet exactly, i.e., there will be a gap on one side of the instrument, or the other, depending on whether the version of the instrument is right or left handed. Because of this gap, one should be able to see "through" the instrument in a limited fashion.

This embodiment would result in a surgical instrument that cuts only on one side, as noted previously. However, it would also allow the production of left and right-handed versions of the instrument, depending on the side selected for cutting. This is quite important because it would allow the versions of the instrument (right or left handed) to be matched to the right or left handedness of the user, generally a surgeon. Additionally, given the precision necessary in modem surgery, it might be useful to only have the cutting occur on a specific side of the instrument, thus allowing the surgeon to completely visualize the cutting operation at all times and assist in cutting the suture or other object as precisely and closely as possible.

To make visual identification of the different versions easier, the instrument could be marked, for instance, by a recognizable surface color on the thumb side, or by other physical features meant to identify whether the instrument is meant to cut on either the right or the left hand side. Although, of course, most users would wish to see the side at which the cutting is taking place, some users will not, and some users will wish to hold the instrument in a "backside" configuration, so that the cutting is taking place on the side than cannot be seen. In fact, some users will find this "backside" cutting position preferable because of their specific hand and forearm pronation ability. In any event, the instrument may be marked by easily observable physical features so that a user can determine quickly which side cuts. This will allow users to quickly select the instrument that is best suited for their specific needs and preferences.

Additionally, the cutting edge or edges can be of any size or configuration. For instance, suture materials that are especially thick or resilient might be severed more easily by a concave cutting edge, and the present invention extends to embodiments having a concave edge or other geometries, such as a notch. Additionally, a cutting edge or edges with serrations can be used, which would also facilitate the cutting action.

The cutting edge or edges can be constructed of material such that they could be re-sharpened, so that the instrument has a long service life. Alternatively, the edge or edges can be replaceable or removable inserts and can be attached to one of the opposing jaws by any attachment means. This would allow the use of replaceable edges. This would allow the instrument to have a long service life.

Furthermore, the instrument may incorporate a transversely disposed stop block S1, as depicted in FIG. 3. The transversely disposed stop block S1 is formed on one of the opposing jaws, between the longitudinally disposed cutting edge 3 and the distal gripping portion 1(FIG. 1), with the other of the opposing jaws being fitted with a recess for receiving the stop block The stop block may be on either of the jaws. This feature makes it even less likely that anything can reach the cutting edge or edges without the knowledge of the user, and adds another margin of safety to the instrument. Additionally, once a suture is slipped over the stop block S1, the suture is "caught" by the stop block and cannot easily move to the distal gripping portion 1, where it would not be cut. Therefore, the addition of the transversely disposed stop block S1 makes it less likely that anything but a suture or other intended object is cut, and also reduces the possibility that a suture will avoid the cutting edge or edges once the user wishes to perform this function.

The instrument described herein can be manufactured of any material having sufficient strength and hardness to serve the intended purpose. The material used herein can be can be the same as with conventional needle holders or scissors. For instance, the instrument may be manufactured of stainless steel, or other metals, or alloys of stainless steel, such as titanium alloys, or composite materials. The instrument may be disposable or sterilizable. The different components of the instrument can be manufactured of the same or different materials. Additionally, the instrument can be manufactured in any size or curvature, as it may be necessary to have different size instruments, depending on the type of surgical application and the size of the needle and the thickness of the suture, and the size of the user's hand. Furthermore, the present invention can be produced either by retrofitting existing needle holders built on a mortise and tenon mechanism to include a cutting edge, or by manufacturing a new instrument.

In summary, the instrument described herein fulfills a long felt need for a combination needle holder and scissors. Use of this instrument allows a user to place and trim sutures without changing instruments, or using two separate instruments. This instrument speeds the process of suturing and reduces the changes of contaminating the sterile field if an instrument is dropped. Additionally, unlike previous designs, the present invention does not present a cutting edge during normal operations, such as grasping and manipulating a surgical needle during suturing. This allows the user to perform suturing without the possibility of exposing sensitive or delicate tissue to a cutting surface, and still allows a suture to be trimmed or severed without placing tension on the suture during the process. Finally, although the most likely use of the present invention is as a dual function needle holder and surgical scissors, the utility of the present invention is not limited merely to grasping needles. The present invention may be used grasp a variety of objects or materials, such as surgical drains, that might be useful in surgical operations or other fields of use, as well as for general grasping or clamping or cutting functions that may be necessary in the practice of surgery.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A medical instrument comprising:
   a first handle pivotally attached to a second handle through a mortise and tenon joint to define opposing jaws at the distal end of the surgical instrument, each of said opposing jaws including a distal gripping portion,
   a longitudinally disposed aperture, situated between said distal gripping portion and said mortise and tenon joint, at least one longitudinally disposed cutting edge situated between said distal gripping portion and said mortise and tenon joint,
wherein said at least one longitudinal disposed cutting edge is adjacent to said mortise and tenon joint and fits within said aperture or said at least one longitudinally disposed cutting edge is formed on at least one side of said aperture or both.

2. The medical instrument of claim 1, wherein said opposing jaws are both movable.

3. The medical instrument of claim 1, wherein said opposing jaws further comprise complementary needle receiving teeth, capable of firmly gripping a surgical needle, on said distal gripping portion of each opposing jaw.

4. The medical instrument of claim 1, further comprising:
a transversely disposed stop block positioned on one of said opposing jaws,
between said at least one cutting edge and said distal gripping portion, the other of said opposing jaws being provided with a recess for receiving the stop block.

5. The medical instrument of claim 1, wherein said at least one longitudinally disposed cutting edge comprises two longitudinally disposed cutting edges that oppose one another, and are offset to extend past one another when said first and second handles are brought toward one another.

6. The medical instrument of claim 1, wherein said distal gripping portion of said opposing jaws is from about 1 centimeter in length to about 20 centimeters in length.

7. The medical instrument of claim 1, wherein said medical instrument is made of stainless steel.

8. The medical instrument of claim 1, wherein said medical instrument is disposable.

9. The medical instrument of claim 1, wherein said medical instrument is formed from a sterilizable material.

10. The medical instrument of claim 1, wherein said first and second handles have opposing finger loops at a proximal end of the medical instrument.

11. The medical instrument of claim 10, wherein said first and second handles have opposing locking mechanisms.

12. The medical instrument of claim 1, wherein each of said opposing jaws comprise a replaceable insert.

13. The medical instrument of claim 1, wherein said opposing jaws further comprise serrated teeth, capable of firmly gripping a metal object, on said distal gripping portion of each opposing jaw.

14. The medical instrument of claim 1, wherein said at least one longitudinal cutting edge cuts only on the right hand side of said medical instrument.

15. The medical instrument of claim 1, wherein said at least one longitudinal cutting edge cuts only on the left hand side of said medical instrument.

16. The medical instrument of claim 1, wherein said at least one longitudinal cutting edge can be re-sharpened.

17. The medical instrument of claim 1, wherein said at least one longitudinal cutting edge is a replaceable insert.

18. The medical instrument of claim 1, wherein said at least one longitudinal cutting edge is serrated.

19. The medical instrument of claim 1, wherein said at least one longitudinal cutting edge is serrated and a replaceable insert.

20. The medical instrument of claim 1, wherein said opposing jaws further comprise complementary receiving teeth.

21. The medical instrument of claim 1, wherein said at least one longitudinally disposed cutting edge comprises a single cutting edge formed on a projection of the tenon of said mortise and tenon joint.

22. The medical instrument of claim 1, wherein said at least one longitudinally disposed cutting edge comprises two longitudinally disposed cutting edges, about parallel to one another, formed on both sides of a projection of the tenon of said mortise and tenon joint.

23. The medical instrument of claim 1, wherein said at least one longitudinally disposed cutting edge comprises a single cutting edge, formed on either side of the aperture.

24. The medical instrument of claim 1, wherein said at least one longitudinally disposed cutting edge comprises two longitudinally disposed cutting edges, roughly parallel to one another, formed on both sides of the aperture.

25. The medical instrument of claim 1, wherein said at least one longitudinally disposed cutting edge comprises: two longitudinally disposed cutting edges, roughly parallel to one another, formed on both sides of the aperture; and two additional longitudinally disposed cutting edges, roughly parallel to one another, formed on both sides of a projection of the tenon of said mortise and tenon joint.

26. The medical instrument of claim 1, wherein said at least one longitudinally disposed cutting edge comprises two pairs of longitudinally disposed cutting edges, wherein each pair of longitudinally disposed cutting edges further comprises two longitudinally disposed cutting edges that oppose one another, and are offset to extend past one another when said first and second bandies are brought toward one another.

27. A medical instrument comprising:
a first handle pivotally attached to a second handle through a mortise and tenon joint having a mortise and tenon, to define opposing jaws at the distal end of the surgical instrument, each of said opposing jaws including a distal gripping portion,
a longitudinally disposed aperture that is part of the mortise, situated between said distal gripping portion and where said mortise and tenon joint are pivotally attached,
at least one longitudinally disposed cutting edge situated between said distal gripping portion and where said mortise and tenon are pivotally attached and said at least one longitudinally cutting edge is part of said mortise or said tenon or both,
wherein said at least one longitudinal disposed cutting edge fits within said aperture or said at least one longitudinally disposed cutting edge is formed on at least one side of said aperture or both.

28. The medical instrument of claim 27, wherein each of said opposing jaws comprise a replaceable insert.

29. The medical instrument of claim 27, further comprising:
a transversely disposed stop block positioned on one of said opposing jaws, between said at least one cutting edge and said distal gripping portion, the other of said opposing jaws being provided with a recess for receiving the stop block.

* * * * *